United States Patent [19]
Liotta et al.

[11] Patent Number: 5,852,027
[45] Date of Patent: Dec. 22, 1998

[54] ANTIVIRAL 1,3-DIOXOLANE NUCLEOSIDE ANALOGUES

[75] Inventors: Dennis C. Liotta, McDonough; Raymond F. Schinazi, Decatur, both of Ga.; Woo-Baeg Choi, North Brunswick, N.J.

[73] Assignee: Emory University, Atlanta, Ga.

[21] Appl. No.: 150,012

[22] PCT Filed: Feb. 21, 1992

[86] PCT No.: PCT/US92/01393

§ 371 Date: Nov. 9, 1993

§ 102(e) Date: Nov. 9, 1993

[87] PCT Pub. No.: WO92/14729

PCT Pub. Date: Sep. 3, 1992

Related U.S. Application Data

[63] Continuation-in-part of Ser. No. 659,760, Feb. 22, 1991, Pat. No. 5,210,085, Ser. No. 803,028, Dec. 6, 1991, Pat. No. 5,276,151, and Ser. No. 736,089, Jul. 26, 1991, abandoned.

[51] Int. Cl.⁶ ........................ A61K 31/505; C07D 239/02
[52] U.S. Cl. ........................... 514/274; 514/467; 514/49; 544/317; 549/429; 536/28.5; 536/28.51; 536/28.52
[58] Field of Search ........................ 435/117, 123, 435/280; 536/28.2; 544/317; 549/429; 514/274, 467

[56] References Cited

U.S. PATENT DOCUMENTS

| | | | |
|---|---|---|---|
| 4,000,137 | 12/1976 | Dvonch et al. | 260/252 |
| 4,140,761 | 2/1979 | Gerin et al. | 514/12 |
| 4,336,381 | 6/1982 | Nagata et al. | 544/313 |
| 4,601,987 | 7/1986 | Klibanov et al. | 435/280 |
| 4,732,853 | 3/1988 | Whitesides et al. | 435/123 |
| 4,861,759 | 8/1989 | Mitsuya et al. | 514/46 |
| 4,879,277 | 11/1989 | Mitsuya et al. | 514/49 |
| 4,900,828 | 2/1990 | Belica et al. | 544/317 |
| 4,916,122 | 4/1990 | Chu et al. | 514/50 |
| 4,923,810 | 5/1990 | Walts et al. | 435/117 |
| 4,963,533 | 10/1990 | de Clercq et al. | 514/49 |
| 5,011,774 | 4/1991 | Farina et al. | 435/87 |
| 5,032,523 | 7/1991 | Amano et al. | 435/280 |
| 5,041,449 | 8/1991 | Belleau et al. | 514/274 |
| 5,041,499 | 8/1991 | Belleau et al. | 514/274 |
| 5,047,407 | 9/1991 | Belleau et al. | 514/274 |
| 5,059,690 | 10/1991 | Zahler et al. | 544/276 |
| 5,071,983 | 12/1991 | Koszalka et al. | 544/317 |
| 5,084,387 | 1/1992 | Patel et al. | 435/123 |
| 5,106,750 | 4/1992 | Wong et al. | 435/280 |
| 5,179,104 | 1/1993 | Chu et al. | 544/310 |
| 5,185,437 | 2/1993 | Koszalka et al. | 536/24 |
| 5,204,466 | 4/1993 | Liotta et al. | 544/317 |
| 5,210,085 | 5/1993 | Liotta et al. | 514/274 |
| 5,234,913 | 8/1993 | Furman, Jr. et al. | 514/49 |
| 5,248,776 | 9/1993 | Chu et al. | 544/310 |

(List continued on next page.)

FOREIGN PATENT DOCUMENTS

| | | |
|---|---|---|
| 665187 | 2/1992 | Australia . |
| 630913 | 9/1992 | Australia . |
| 0217580 | 4/1987 | European Pat. Off. . |
| 0352248 | 7/1989 | European Pat. Off. . |
| 0337713 | 10/1989 | European Pat. Off. . |
| 350 811 | 1/1990 | European Pat. Off. . |
| 357 009 | 3/1990 | European Pat. Off. . |
| 361 831 | 4/1990 | European Pat. Off. . |
| 0375329 | 6/1990 | European Pat. Off. . |
| 0382526 | 8/1990 | European Pat. Off. . |
| 421 636 | 4/1991 | European Pat. Off. . |
| 0433898 | 6/1991 | European Pat. Off. . |
| 0494119 | 7/1992 | European Pat. Off. . |
| 0515144 | 11/1992 | European Pat. Off. . |
| 0515156 | 11/1992 | European Pat. Off. . |
| 0515157 | 11/1992 | European Pat. Off. . |
| 0526253 | 2/1993 | European Pat. Off. . |
| 2-69469 | 3/1990 | Japan . |
| 2-69476 | 3/1990 | Japan . |
| 07109221 | 4/1995 | Japan . |
| 8901258 | 12/1990 | Netherlands . |
| 238017 | 6/1994 | New Zealand . |
| WoO 88/07532 | 10/1988 | WIPO . |
| WO 90/12023 | 10/1990 | WIPO . |
| WO 91/11186 | 8/1991 | WIPO . |
| WO 91/17159 | 11/1991 | WIPO . |
| WO92/08717 | 5/1992 | WIPO . |
| WO92/08727 | 5/1992 | WIPO . |
| WO 92/10496 | 6/1992 | WIPO . |
| WO 92/10497 | 6/1992 | WIPO . |

(List continued on next page.)

OTHER PUBLICATIONS

U.S. application No. 07/686,617, Cheng et al., filed Jul. 1996.
U.S. application No. 07/718,806, Cheng, filed Jun. 1991.
U.S. application No. 07/785,545, Cheng, filed Oct. 1991.
Abobo, et al., "Pharmacokinetics of 2',3'-Dideoxy-5-fluoro-3'-thiacytidine in Rats," *J. of Pharmaceutical Sciences*, 83(1):96–99 (1994). Month of Publication data is unavailable. Issue No. has been included when possible.
Agranat and Biedermann, "Intellectual Property and Chirality: Patentability of Enantiomers of Racemic Drugs in a Racemic Switch Scenario,"*8th Chirality Conference, Edinburgh, UK* (Jul. 2, 1996).

(List continued on next page.)

*Primary Examiner*—John Kight
*Assistant Examiner*—L. Eric Crane
*Attorney, Agent, or Firm*—Sherry M. Knowles; Jacqueline Haley; King & Spalding

[57] ABSTRACT

This invention includes the compounds 2'-deoxy-5-fluoro-3'-oxacytidine, (−)-2'-deoxy-5-fluoro-3'-oxacytidine, and (+)-2'-deoxy-5-fluoro-3+-oxacytidine, and pharmaceutically acceptable salts thereof for use in medical therapy, for example for the treatment or prophylaxis of an HIV infection.

7 Claims, 2 Drawing Sheets

U.S. PATENT DOCUMENTS

| | | | |
|---|---|---|---|
| 5,270,315 | 12/1993 | Belleau et al. | 514/262 |
| 5,276,151 | 1/1994 | Liotta et al. | 544/317 |
| 5,444,063 | 8/1995 | Schinazi | 514/262 |
| 5,466,806 | 11/1995 | Belleau et al. | 544/310 |
| 5,486,520 | 1/1996 | Belleau et al. | 514/374 |
| 5,532,246 | 7/1996 | Belleau et al. | 514/374 |
| 5,538,975 | 7/1996 | Dionne | 514/274 |
| 5,539,116 | 7/1996 | Liotta et al. | 544/317 |
| 5,587,480 | 12/1996 | Belleau et al. | 544/310 |
| 5,618,820 | 4/1997 | Dionne | 514/256 |

FOREIGN PATENT DOCUMENTS

| | | |
|---|---|---|
| WO 92/14729 | 9/1992 | WIPO . |
| WO 92/14743 | 9/1992 | WIPO . |
| WO 92/15308 | 9/1992 | WIPO . |
| WO92/14729 | 9/1992 | WIPO . |
| WO92/15309 | 9/1992 | WIPO . |
| WO 92/18517 | 10/1992 | WIPO . |
| WO 92/21676 | 12/1992 | WIPO . |
| WO94/04154 | 3/1994 | WIPO . |
| WO94/09793 | 5/1994 | WIPO . |
| WO 94/14456 | 7/1994 | WIPO . |
| WO94/14802 | 7/1994 | WIPO . |
| WO 94/27616 | 12/1994 | WIPO . |
| WO 95/18137 | 7/1995 | WIPO . |
| WO 95/21183 | 8/1995 | WIPO . |

OTHER PUBLICATIONS

Baschang, et al., "The enantiomers of 1.beta.–adenyl–2.alpha.–hydroxy–3.beta.–(hydroxymethyl)cyclobutane," *Tetrahedron:Asymmetry*, 3(2):193–6 (1992), Abstr. Only. Month of Publication data is unavailable. Issue No. has been included when possible.

Chu, et al., "Synthesis and Anti–HIV and Anti–HBV Activity of Enantiomerically Pure Oxathiolane Nucleosides," *Antiviral Research*, 17(S1):44 (1992). Month of Publication data is unavailable. Issue No. has been included when possible.

Chu, et al., "Synthesis and Biological Evaluation of D–(2S) and L–(2R)–1,3–Oxathiolanyl–and D–(2R)–and L–(2S)–1,3–Dioxolanyl–Nucleosides as Anti–HIV and Anti–HBV Agents," *Antiviral Research*, 20(S1):146 (1993), Abstr No. 192. Month of Publication data is unavailable. Issue No. has been included when possible.

Condreay, et al., "Evaluation of the Potent Anti–Hepatitis B Virus Agent (–) cis–5–Fluoro–1–[2–(Hydroxymethyl)–1,3–Oxathiolan–5–yl]Cytosine in a Novel In Vivo Model," *Antimicrobial Agents and Chemotherapy*, 616–619 38 (3), (Mar. 1994). Month of Publication data is unavailable. Issue No. has been included when possible.

Connolly and Hammer, "Minireview: Antiretroviral Therapy: Reverse Transcriptase Inhibition," *Antimicrobial Agents and Chemotherapy*, 36(2):245–254 (1992). Month of Publication data is unavailable. Issue No. has been included when possible.

Feorino et al., "Prevention of activation of HIV–1 by antiviral agents in OM–10.1 cells," *Antiviral Chem. & Chemotherapy*, 4(1):55–63 (1993). Month of Publication data is unavailable. Issue No. has been included when possible.

Frick, et al., "Pharmacokinetics, Oral Bioavailability, and Metabolic Disposition in Rats of (–)–cis–5–Fluoro–1–[2–Hydroxymethyl)–1,3–Oxathiolan–5–yl]Cytosine, a Nucleoside Analog Active against Human Immunodeficiency Virus and Hepatitis B Virus," *Antimicrobial Agents and Chemotherapy*, 38(12):2722–2724 (1994). Month of Publication data is unavailable. Issue No. has been included when possible.

Furman, et al., "Phosphorylation of 3'–azido–3'–deoxythymidine and selective interaction of the 5'–triphosphate with human immunodeficiency virus* reverse transcriptase," *Proc. Natl. Acad. Sci. USA*, 83:8333–8337 (1986) (Nov.).

Hoong et al., "Enzyme–Mediated Enantioselective Preparation of Pure Enantiomers of the Antiviral Agent 2',3'–Dideoxy–5–fluoro–3'–thiacytidine (FTC) and Related Compounds," *J. Org. Chem.*, 57:5563–5565 (1992). Month of Publication data is unavailable. Issue No. has been included when possible.

Ito, et al., "Chirally Selective Synthesis of Sugar Moiety of Nucleosides by Chemicoenzymatic Approach: L–and D–Riboses, Showdomycin, and Cordycepin," *J. Am. Chem. Soc.*, 103:6739–6741 (1981) (issue No. 22). Month of Publication data is unavailable. Issue No. has been included when possible.

Jansen, et al., "High–Capacity In Vitro Assessment of Anti–Hepatitis B Virus Compound Selectivity by a Virion–Specific Polymerase Chain Reaction Assay," *Antimicrobial Agents and Chemotherapy*, pp. 441–447 vol. 37, No. 3 (Mar. 1993).

Kim, et al., "Asymmetric Synthesis of 1,3–Dioxolane–Pyrimidine Nucleosides and Their Anti–HIV Activity," *J. Med. Chem.*, 35:1987–1995 (1992) (issue No. 11). Month of Publication date is unavailable. Issue No. has been included when possible.

Kim, et al., "Potent Anti–HIV and Anti–HBV Activities of (–)–L–β–Dioxolane–C and (+)–L–β–Dioxolane–T and Their Asymmetric Syntheses," *Tetrahedron Lett.*, 33(46):6899–6902 (1992). Month of Publication data is unavailable. Issue No. has been included when possible.

Martin, et al., "Synthesis and Antiviral Activity of Monofluoro and Difluoro Analogues of Pyrimidine Deoxyribonucleosides against Human Immunodeficiency Virus (HIV–1)," *J. Med. Chem.*, 33:2137–2145 (1990) (issue No. 8). Month of Publication data is unavailable. Issue No. has been included when possible.

Ohno, et al., "Synthetic Studies on Biologically Active Natural Products by a Chemicoenzymatic Approach," *Tet. Letters*, 40:145–152 (1984) (issue No. 1). Month of Publication data is unavailable. Issue No. has been included when possible.

Paff, et al., "Intracellular Metabolism of (–)–and (+)–cis–5–Fluoro–1–[2–Hydroxymethyl)–1,3–Oxathiolan–5–yl]Cytosine in HepG2 Derivative 2.2.15 (Subclone P5A)Cells," *Antimicrobial Agents and Chemotherapy*, 1230–1238 (1994), vol. 38, Issue No. 6 (Jun.).

Roberts et al., "Enzymic Resolution of cis–and trans–4–hydroxycyclopent–2–enylmethanol . . . " *J. Chem.. Soc.*, Perkin Trans. 1, (10:2605–7 (1991). Month of Publication data is unavailable. Issue No. has been included when possible.

Saari, et al., "Synthesis and Evaluation of 2–Pyridinone Derivatives as HIV–1–Specific Reverse Transcriptase Inhibitors, 2. Analogues of 3–Aminopyridin–2(1H)–one," *J. Med. Chem.*, 35:3792–3802 (1992) (issue No. 21). Month of Publication data is unavailable. Issue No. has been included when possible.

Saunders, "Non–Nucleoside Inhibitors of HIV Reverse Transcriptase: Screening Successes–Clinical Failures," *Drug Design and Discovery*, 8:255–263 (1992). Month of Publication data is unavailable. Issue No. has been included when possible.

Shewach, et al., "Affinity of the antiviral enantiomers of oxathiolane cytosine nucleosides for human 2'–deoxycytidine kinase," *Biochem. Pharmacol.*, 45(7):1540–1543 (1993). Month of Publication data is unavailable. Issue No. has been included when possible.

van Roey, et al., "Solid State Conformation of Anti–Human Immnosudeficiency Virus Type–1 Agents: Crystal Structures of Three 3'–Azido–3'–deoxythymidine Analogues," *J. Am Chem. Soc.*, 110:2277–2782 issue No. 7 (Mar. 30, 1988).

Wilson, et al., "The 5'–Triphosphates of the (1) and (+) Enantiomers of cis–5–Fluoro–1–[2–(Hydroxymethyl)–1, 3–Oxathiolane–5–yl]Cytosine Equally Inhibit Human Immunodeficiency Virus Type 1 Reverse Transcriptase," *Antimicrob. Agents and Chemother.*, 37(8):1720–1722 (Aug., 1993).

Winslow, et al., "In vitro susceptibility of clinical isolates of HIV–1 to XM323, a non–peptidy HIV protease inhibitor," *AIDS*, 8:753–756 issue No. 6 (Jun. 1994).

*Journal of Acquired Immune Deficiency Syndromes*, (Raven Press, Publisher), vol. 6, (1), 24–31 (Jan. 1993), Lai et al., "Impeded Progression of Friend Disease in Mice by an Inhibitor of Retroviral Proteases.".

Borthwick, et al., "Synthesis and Enzymatic Resolution of Carbocyclic 2'–Ara–Fluoro–Guanosine: A Potent New Anti–Hepetic Agent," *J. Chem. Soc. Commun.*, Issue No. 10. pp.656–658 (1988). Month of publication date is unavailable. Issue No. has been supplied whenever possible.

Herdewijn, et al., "Resolution of Aristeromycin Enantiomers," *J. Med. Chem.*, 1985, vol. 28, 1385–1386–(Issue No. 10).

Krenitsky, et al., "An Enzymic Synthesis of Purine D-arabinonucleosdes," *Carbohydrate Research*, vol. 97, pp. 139–146 (1981). Month of publication data is unavailable. Issue No. has been supplied whenever possible.

Mahmoudian, et al., "Enzymatic Production of Optically Pure (2'R–cis)–2'–deoxy–3'–thiacytidine (3TC, Lamivudine): A Potent Anti–HIV Agent," *Enzyme Microb. Technol.*, Sep. 1993, vol. 15, 749–755, published by the Glaxo Group Research Ltd. (Sep.).

Pirkle and Pochansky, "Chiral Stationary Phases for the Direct LC Separation of Enaniomers," *Advances in Chromatography*, Giddings, J.C., Grushka, E., Brown, P.R., eds.: Marcel Dekker: New York, 1987; vol. 27, Chap. 3, pp. 73–127. Month of publication data is unavailable. Issue No. has been supplied whenever possible.

Secrist, et al., "Resolution of Racemic Carbocyclic Analogues of Purine Nucleosides Through the Action of Adenosine Deaminase Antiviral Activity of the Carbocyclic 2'–Deoxyguanosine Enantiomers," *J. Med. Chem.*, vol. 30, pp. 746–749 (1987) (Issue No. 4). Month of publication data is unavailable. Issue No. has been supplied whenever possible.

Fukunaga et al., "Hypotensive Effects of Adenosine and Adenosine Triphosphate Compared with Sodium Nitroprusside," *Anesthesia and Analgesia*, 61(3), 273–278 (1982).

Chu, et al., "Asymmetric Synthesis of Enantiomerically Pure (–)–'R,4'R)–Dioxolane–thymine and Its Anti–HIV Activity," *Tetrahedron Letters*, 32(31):3791–3794 (1991).

Balzarini, J., et al., "Potent and Selective Anti–HTLV–III/LAV Activity of 2',3'Dideoxycytidinen, the 2', 3'–Unsaturated Derivative of 2',3'–Dideoxycytidine," *Biochemical and Biophysical Research Communications*, 140(2): 735–742 (1986) (Oct.).

Belleau, B., et al., "Design and Activity of a Novel Class of Nucleoside Analogs Effective Against HIV–I," *International Conference on AIDS*, Montreal, Quebec, Canada, Jun. 4–9, 1989.

Carter, et al., "Activities of (–)–Carbovir and 3'–Azido–3'–Deoxythymidine Against Human Immunodeficiency Virus in Vitro," *Antimicrobial Agents and Chemotherapy*, 34(6):1297–1300 (1990) (Jun.).

Chang, et al., "Deoxycytidine Deaminase–resistant Steroisomer Is the Active Form of (+)–2', 3'–Dideoxy–3'–thiacytidine in the Inhibition of Hepatitis B Virus Replication," *The Journal of Biological Chemistry*, 267(20):13938–13942 (1992) (Jul.).

Chang, Chungming, et al., "Production of Hepatitis B Virus In Vitro by Transient Expression of Cloned HBV DNA in a Hepatoma Cell Line," *The EMBO Journal*, 6(3):675–680 (1987). Month of publication data is unavailable. Issue No. has been included whenever possible.

Chen, Chin–Ho, et al., "Delayed Cytotoxicity and Selective Loss of Mitochondrial DNA in Cells Treated with the Anti–Human Immunodeficiency Virus Compound 2',3'–Dideoxycytidine," *The Journal ofbiological Chemistry*, 264(20):1193411937 (1989) (Jul.).

Chu, C.K., et al., "An Efficient Total Synthesis of 3'–Azido–3'–Deoxythiymidine (AZT) and 3',–Azido–2', 3'–Dideoxyuridine (AZDDU. CS–87) from D–Mannitol," *Tetrahedron Lett.*, 29(42):5349–5352 (1988). Month of publication data is unavailable. Issue No. has been included whenever possible.

Chu, et al., "Comparative Activity of 2',3'–Saturated and Unsaturated Pyrimidine and Purine Nucleosides Against Human Immunodeficiency Virus Type I in Peripheral Blood Mononuclear Cells," *Biochem. Pharm.*, 37(19):3543–3548 (1988). Month of publication data is unavailable. Issue No. has been included whenever possible.

Chu, et al., "Structure–Activity Relationships of Pyrimidine Nucleosides as Antiviral Agents for Human Immunodeficiency Virus Type I in Peripheral Blood Mononuclear Cells," *J Med Chem.*, 32:612 (1989) (Issue No. 3). Month of publication data is unavailable. Issue No. has been included whenever possible.

Cretton, F., et al., "Catabolism of 3'–Azido–3'–Deoxythymidine in Heptaocytes and Liver Microsomes, with Evidence of Formation of 3'–Amino–3'–Amino–3'Deoxythymidine, a Highly Toxic Catabolite for Human Bone Marrow Cells," *Molecular Pharmacology*, 39:258–266 (1991). Month of publication data is unavailable. Issue No. has been included whenever possible.

Cretton, E., et al., "Pharmokinetics of 3'–Azido–3'–Deoxythymidine and its Catabolites and Interactions with Probenecid in Rhesus Monkeys," *Antimicrobial Agents and Chemotherapy*, 35(5):801–807 (1991) (May).

Di Bisceglie, Adrian M., Rustgi, Vinod K. et al., "Hepatocellular Carcinoma," *NIH Conference, Annals of Internal Medicine*, 108:390–401 (1988) (Mar.).

Doong, Shin–Lian., et al., "Inhibition of the Replication of Hepatitis B Virus in vitro by 2',3'–Dideoxy–3'–Thiacytidine and Related Analogues," *Natt. Acad Sci, USA*, 88:8495–8499 (1991) (Oct.).

Evans, David A., et al., I "New Procedure for the Direct Generation of Titanium Enolates. Diastereoselectie Bond Constructions with Representative Electrophiles," *J. Am. Chem. Soc.*, 112:8215–8216 (1990). Month of publication data is unavailable. Issue No. has been included whenever possible.

Furman, et al., "The Anti–Hepatitis B Virus Activities, Cytotoxicities, and Anabolic Profiles of the (−) and (+) Enantiomers of cis–5–Fluoro–1[2(Hydromethyl)–1, 3–Oxthiolane–5–yl]Cytosine," *Antimicrobial Agents and Chemotherapy*, 36(12):2686–2692 (1992) (Dec.).

Ganem, Don et al., "The Molecular Biology of the Hepatitis B Viruses," *Ann. Rev. Biochem.*, 56:651–693 (1987). Month of publication data is unavailable. Issue No. has been included whenever possible.

Jeong, L., et al., "Asymmetric Synthesis and Biological Evaluation of B–L(2R,5S)–and a –L–(2R–5R)–1,3 –Oxathiolane–Pyrimidine and –Purine Nucleosides and Potential Anti–HIV Agents," *J Med Chem.*, 36(2):181–195 (1993) (Jan.).

Kassianides, Chris, et al, "Inhibition of Duck Hepatitis B Virus Replication by 2',3'–Dideoxycytidine," *Gastroenterology*, 97(5):1275–1280 (1989) (Nov.).

Kim, Hea O., et al., "L–β–(2S,4S)– and L–α–(2S,4R)–Dioxolanyl Nucleosides and Potential Anti–HIV Agents: Asymmetric Synthesis and Structure–Activity Relationships," *J Med Chem.*, 36(5):519–528 (1993) (Mar.).

Kim, Hea O., et al., "1,3–Dioxolanylpurine Nucleosides (2R,4R) and (2R,4S) with Selective Anti–HIV–1 Activity in Human Lymphocytes," *J Med Chem.*, 36:30–37 (1993) (Issue No. 1, Jan.).

Krenitsky, T.A., et al., "3'–Amino–2',3'–Dideoxyribonucleosides of Some Pyrimidines: Synthesis and Biological Activities," *J Med Chem.*, vol. 26 (1983), Issue No. 6, pp. 891–895. Month of publication data is unavailable. Issue No. has been included whenever possible.

Lee, Bonita, et al. "In Vitro and In Vivo Comparison of the Abilities of Purine and Pyrimidine 2',3'–Dideoxynucleosides To Inhibit Duck Hepadnavirus," *Antimicrobial Agents and Chemotherapy*, 33(3):336–339 (1989) (Mar.).

Lin, et al, "Potent and Selective In Vitro Activity of 3'–Deoxythmindin–2'–Ene(3'–Deoxy–2',3'–Didehydrothymidine) Against Human Immunodeficiency Virus," *Biochem. Pharm.*, 36(17):2713–2718 (1987) (Sep.).

Matthes, E., et al., "Potent Inhibition of Hepatitis B Virus Production In Vitro by Modified Pyrimidine Nucleosides," *Antimicrobial Agents and Chemotherapy*, 34(10):1986–1990 (1990) (Oct.).

Miller, Roger H., et al., "Common Evolutionary Origin of Hepatitis B Virus and Retroviruses," *Proc. Natl. Acad Sci. USA*, 83:2531–2535 (1986) (Apr.).

Mitsuya, H., et al., 3'–Azido–3'–Deoxythymidine (BW A 509U): An Antiviral Agent that Inhibits the Infectivity and Cytopathic Effect of Human T–Lymphotropic Virus Type III/Lymphadenopathy–Associated Virus In Vitro, *Proc. Natl. Acad. Sci., USA*, 82:7096–7100 (1985) (Oct.).

Mitsuya, H., et al., "Molecular Targets for AIDS Therapy," *Science*, vol. 249, pp. 1533–1544 (1990) (Sep.).

Mitsuya, H., et al., "Rapid in Vitro Systems for Assessing Activity of Agents Against HTLV–III/LAV," *AIDS: Modern Concepts and Therapeutic Challenges*, S. Broder, Ed. pp. 303–333, Marcel–Dekker, New York (1987). Month of publication data is unavailable. Issue No. has been included whenever possible.

Norbeck, D., et al., "A New 2',3'–Dideoxynucleoside Prototype with In Vitro Activity Against HIV," *Tetrahedron Lett.*, 30(46):6263–6266 (1989). Month of publication data is unavailable. Issue No. has been included whenever possible.

Okabe, M., et al., "Synthesis of the Dideoxynucleosides ddC and CNT from Glutamic Acid, Ribonolactone, and Pyrimidine Bases," *J Org. Chem.*, 53(20):4780–4786 (1988). Month of publication data is unavailable. Issue No. has been included whenever possible.

Richman, D.D., et al., "The Toxicity of Azidothymidine (A.ZT) in the Treatment of Patients with AIDS and AIDS–Related Complex," *N. Eng. J Med*, 317(4):192197 (1987) (Jul.).

Satsumabayashi, S. et al., "The Synthesis of 1,3–Oxathiolane–5–one Derivatives," *Bull. Chem. Soc. Japan*, 45:913–915 (1972) (Mar.).

Schinazi, R.F., et al., "Activities of the Four Optical Isomers of 2',3'–Dideoxy–3'–Thiacytidine (BCH–1 89) against Human Immunodeficiency Virus Type I in Human Lymphocytes," *Antimicrobial Agents and Chemotherapy* 36(3):672–676 (1992) (May).

Schinazi, R.F., et al., "Insights into HIV Chemotherapy," *AIDS Research and Human Retroviruses* 8(6):963–990 (1992). Month of publication data is unavailable. Issue No. has been supplied whenever possible.

Schinazi, R.F., et al., "Pharmacokinetics and Metabolism of Racemic 2',3'–Dideoxy–5–Fluoro–3'–Thiacytidine in Rhesus Monkeys," *Antimicrobial Agents and Chemotherapy* 36(11):2432–2438 (1992) (Nov.).

Schinazi, R.F., et al., "Selective Inhibition of Human Immunodeficiency Viruses by Racemates and Enantiomers of cis–5–Fluoro–1–[2–(Hydroxymethyl)–1,3Oxathiolan–5–yl] Cytosine," *Antimicrobial Agents and Chemotherapy* 36(11):2423–2431 (1992) (Nov.).

Schinazi, R.F., et al., "Substrate Specificity of *Escherichia Coli* Thymidine Phosphorylase for Pyrimidine Nucleoside with an Anti–Human Immunodeficiency Virus Activity," *Biochemical Pharmacology* 44(2):199–204 (1992). Month of publication data is unavailable. Issue No. has been included whenever possible.

Sells, Mary Ann, et al, "Production of Hepatitis B Virus Particles in Hep G2 Cells Transfected with Cloned Hepatitis B Virus DNA," *Proc. Natl. Acad Sci. USA*, 84:1005–1009 (1987) (Feb.).

Soudeyns, H., et al., "Anti–Human Immunodeficiency Virus Type I Activity and In Vitro Toxicity of 2'–Deoxy–3'–Thiacytidine (BCH–1 89), a Novel Heterocyclic Nucteoside Analog," *Antimicrobial Agents and Chemotherapy*, 35(7):1386–1390 (1991) (Jul.).

Sterzycki, R.Z., et al., "Synthesis and Anti–HIV Activity of Several 2'–FluoroContaining Pyrimidine Nucleosides," *J. Med Chem.*, 33(8):2150–2157 (1990). Month of publication data is unavailable. Issue No. has been included whenever possible.

Storer, R., et al., "the Resolution and Absolute Stereochemistry of the Enantiomers of cis–1–2–(Hydromethyl)–1,3–Oxathiolan–5–yl)Cytosine (BCH189): Equipotent Anti–HIV Agents," *Nucleosides & Nucleotides*, 12(2):225–236 (1993). Month of publication data is unavailable. Issue No. has been included whenever possible.

Sureau, C., et al., "Production of Hepatitis B Virus by a Differentiated Human Hepatoma Cell Line after Transfection with Cloned Circular HBV DNA," *Cell*, 47:37–47 (1986) (Oct.).

Tsurimoto, Toshiki et al., "Stable Expression and Replication of Hepatitis B Virus Genome in an Integrated State in a Human Hepatoma Cell Line Transfected with the Cloned Viral DNA," *Proc. –Natl. Acad. Sci. USA*, 84:444–448 (1987) (Jan.).

Volk, Wesley A., editor, "Hepatitis," *Essentials of medical Microbiology*, J.B. Lippincott Company, (Philadelphia/Toronto), 2nd Ed., pp. 609–618 (1982). Month of publication data is unavailable. Issue No. has been included whenever possible.

Vorbriiggen, et al, "Nucleoside Synthesis with Trimethylsilyl Triflate and Perchlorate as Catalysts," *Chem. Ber.*, 114:1234–1255 (1981). Month of publication data is unavailable. Issue No. has been included whenever possible.

Wilson, L.J., et al., "A General Method for Controlling Glycosylation Stereochemistry in the Synthesis of 2'–Deoxyribose Nucleosides," *Tetrahedron Lett.*, 31(13):1815–1818 (1990). Month of publication data is unavailable. Issue No.has been included whenever possible.

Wilson, L.J., et al., "The Synthesis and Anti–HIV Activity of Pyrimidine Dioxolanyl Nucleosides," *Bioorganic & Medicinal Chemistry Letters*, 3(2):169–174 (1993). Month of publication data is unavailable. Issue No. has been included whenever possible.

World Health Organization, "Progress in the Control of Viral Hepatitis: Memorandum from a WHO Meeting," *Bulletin of the World Health Organization*, 66(4):443–455 (1988). Month of publication data is unavailable. Issue No. has been included whenever possible.

Yokota et al., "Comparative Activities of Several Nucleoside Analogs Against Duck Hepatitus B Virus In Vitro," *Antimicrobial Agents and Chemotherapy*, 34(7):1326–1330 (1990) (Jul.).

Zhu, Zhou, et al., "Cellular Metabolism of 3'–Azido–2',3'–Dideoxyuridine with Formation of 5'–O–Diphosphohexose Derivatives by Previously Unrecognized Metabolic Pathways of 2'–Deoxyuridine Analogs," *Molecular Pharmacology*, 38:929–938 (1990). Month of publication data is unavailable. Issue Number has been included whenever possible.

1, 3 - Dioxolane Nucleoside wherein:

B = purine or pyrimidine base
    X = C4' chiral carbon atom
    Y = C1' chiral carbon atom

ANTIVIRAL 1,3-DIOXOLANE NUCLEOSIDE ANALOGUES

BACKGROUND OF THE INVENTION

This application claims priority to International Publication No. WO 92/14729, which is a continuation-in-part of U.S. Ser. No. 07/659,760, filed Feb. 22, 1991, now U.S. Pat. No. 5,210,085; U.S. Ser. No. 07/736,089, filed Jul. 26, 1991, now abandoned; and U.S. Ser. No. 07/803,028, filed Dec. 6, 1991, now U.S. Pat. No. 5,276,151.

The U.S. Government has rights in this invention arising out of National Institutes of Health Grant No. AI-28731 and No. AI-26055.

The invention described herein includes a stereoselective synthesis of 1,3-dioxolane nucleosides, and antivirally active 1,3-dioxolane nucleosides.

In 1981, acquired immune deficiency syndrome (AIDS) was identified as a disease that severely compromises the human immune system, and that almost without exception leads to death. In 1983, the etiological cause of AIDS was determined to be the human immunodeficiency virus (HIV). In December, 1990, the World Health Organization estimated that between 8 and 10 million people worldwide were infected with HIV, and of that number, between 1,000,000 and 1,400,000 were in the United States.

In 1985, it was reported that the synthetic nucleoside 3'-azido-3'-deoxythymidine (AZT) inhibits the replication of human immunodeficiency virus type 1. Since then, a number of other synthetic nucleosides, including 2',3'-dideoxyinosine (DDI), 2',3'-dideoxycytidine (DDC), 3'-fluoro-3'-deoxythymidine (FLT), 2',3'-dideoxy,2',3'-didehydrothymidine (D4T), and 3'-azido-2',3'-dideoxyuridine (AZDU), have been proven to be effective against HIV. A number of other 2',3'-dideoxynucleosides have been demonstrated to inhibit the growth of a variety of other viruses in vitro. It appears that, after cellular phosphorylation to the 5'-triphosphate by cellular kinases, these synthetic nucleosides are incorporated into a growing strand of viral DNA, causing chain termination due to the absence of the 3'-hydroxyl group.

Both DDC and D4T are potent inhibitors of HIV replication with activities comparable (D4T) or superior (DDC) to AZT. However, both DDC and D4T are not efficiently converted to the corresponding 5'-triphosphates in vivo and are resistent to deaminases and phosphorylases. Both compounds are also toxic.

The success of various 2',3'-dideoxynucleosides in inhibiting the replication of HIV in vivo or in vitro has led a number of researchers to design and test nucleosides that substitute a heteroatom for the carbon atom at the 3'-position of the nucleoside. Norbeck, et al., disclose that (±)-1-[(2β,4β)-2-(hydroxymethyl)-4-dioxolanyl]thymine (referred to below as (±)-dioxolane-T or DOT, see FIG. 2), a 1,3 dioxolane nucleoside, exhibits a modest activity against HIV ($EC_{50}$ of 20 μm in ATH8 cells), and is not toxic to uninfected control cells at a concentration of 200 μm. *Tetrahedron Letters* 30 (46), 6246, (1989). In light of the fact that this compound exhibits efficacy against HIV and has very low toxicity, it is desirable to develop suitable synthetic protocols for preparing a wide variety of analogs and isomers of this compound.

To market a nucleoside for pharmaceutical purposes, it must not only be efficacious with low toxicity, it must also be cost effective to manufacture. An extensive amount of research and development has been directed toward new, low cost processes for large scale nucleoside production.

2',3'-Dideoxynucleosides are currently prepared by either of two routes; derivatization of an intact nucleoside or condensation of a derivatized sugar moiety with a heterocyclic base. Although there are numerous disadvantages associated with obtaining new nucleoside analogues by modifying intact nucleosides, a major advantage of this approach is that the appropriate absolute stereochemistry has already been set by nature. Obviously, this approach cannot be used in the production of nucleosides that contain either nonnaturally occurring bases or nonnaturally occurring carbohydrate moieties (and which therefore are not prepared from intact nucleosides), such as 1,3-dioxolane nucleosides.

When condensing a carbohydrate-like moiety such as a 1,3-dioxolane with a heterocyclic base to form a synthetic nucleoside, a nucleoside is produced that has two chiral centers (at the C1' and C4' positions, see FIG. 1), and thus exists as a diastereomeric pair. Each diastereomer exists as a set of enantiomers. Therefore, the product is a mixture of four enantiomers. It is often found that nucleosides with nonnaturally-occurring stereochemistry in either the C1' or the C4'-positions are less active than the same nucleoside with the stereochemistry as set by nature.

It is well known in the art that the stereoselective introduction of bases to the anomeric centers of carbohydrates can be controlled by capitalizing on the neighboring group participation of a 2-substituent on the carbohydrate ring [*Chem. Ber.* 114: 1234 (1981)]. However, dioxolanes do not possess an exocyclic 2-substituent and, therefore, cannot utilize this procedure unless additional steps to introduce a functional group that is both directing and disposable are incorporated into the synthesis. These added steps would lower the overall efficiency of the synthesis.

It is also well known in the art that "considerable amounts of the undesired α-nucleosides are always formed during the synthesis of 2'-deoxyribosides" [*Chem. Ber.* 114: 1234, 1244 (1981)]. Furthermore, this reference teaches that the use of simple Friedel-Crafts catalysts like $SnCl_4$ in nucleoside syntheses produces undesirable emulsions upon the workup of the reaction mixture, generates complex mixtures of the α and β-isomers, and leads to stable δ-complexes between the $SnCl_4$ and the more basic silylated heterocycles such as silylated cytosine. These complexes lead to longer reaction times, lower yields, and production of the undesired unnatural N-3-nucleosides.

Therefore, it is an object of the present invention to provide a method for the synthesis of a variety of 1,3-dioxolane nucleosides that includes condensing a 1,3-dioxolane moiety with a purine or pyrimidine base through a process that provides high β-stereoselectivity at the C1' position.

It is another object of the present invention to provide a method for the resolution of racemic mixtures of 1,3-dioxolane nucleosides at the C4'-position.

It is another object of the present invention to provide new antiviral agents, pharmaceutical compositions, and methods of treatment.

SUMMARY OF THE INVENTION

The invention as disclosed includes a method for the synthesis of 1,3-dioxolane nucleosides that includes condensing a suitably protected 1,3-dioxolane moiety with a heterocyclic base, typically a purine or pyrimidine base, to provide a 1,3-dioxolane nucleoside with high β-stereoselectivity in the C1'-position. The method can be used to prepare the $C_1$-β anomer of biologically active 1,3-dioxolane nucleosides such as 2'-deoxy-5-fluoro-3'- oxacytidine (FDOC), 2'-deoxy-3'-oxacytidine (DOC), and 2'-deoxy-3'-oxathymidine (DOT). The method includes condensing a protected 1,3-dioxolane with a suitably protected purine or pyrimidine base in the presence of a titanium-based Lewis acid of the structure:

$$TiX_nY_{m-n}$$

wherein m=4; n=2, 3, or 4; Ti=titanium; X=Cl, Br, or I; and Y is alkoxy, aryloxy, amino, alkylanino, dialkylamino, mixtures thereof, or a bifunctional molecule that contains both an alkoxy and an amino functional group and that is bound to the titanium molecule by both the alkoxy and amino moieties.

A process for the resolution of a racemic mixture of 1,3-dioxolane nucleoside enantiomers is also disclosed that includes the step of exposing the racemic mixture to an enzyme that preferentially catalyzes a reaction in one of the enantiomers. The process can be used to resolve a wide variety of 1,3-dioxolane nucleosides, including pyrimidine and purine nucleosides that are optionally substituted in the carbohydrate moiety or base moiety. The resolution of 1,3-dioxolane nucleosides can be performed on large scale at moderate cost.

A number of 1,3-dioxolane nucleosides described herein have antiviral activity, including anti-HIV activity. The anti-viral activity of the described nucleosides can be evaluated by the method described herein, or as otherwise known to those skilled in the art.

This invention includes:

the compounds (±)-2'-deoxy-5-fluoro-3'-oxacytidine, (–)-2'-deoxy-5-fluoro-3'-oxacytidine, and (+)-2'-deoxy-5-fluoro-3'-oxacytidine;

(±)-β-D,L-2'-deoxy-5-fluoro-3'-oxacytidine, its (–) and (+) enantiomers, and pharmaceutically acceptable derivatives and salts thereof for use in medical therapy, for example for the treatment or prophylaxis of an HIV infection;

and use of (±)-β-D,L-(±)-β-D,L-2'-deoxy-5-fluoro-3'-oxacytidine, its (–) and (+) enantiomers, and pharmaceutically acceptable derivatives and salts thereof in the manufacture of a medicament for treatment of a HIV infection.

DETAILED DESCRIPTION OF THE INVENTION

As used herein, the term "enantiomerically enriched nucleoside" refers to a nucleoside composition that includes at least 95% of a single enantiomer of that nucleoside.

As used herein, the term FDOC refers to 2'-deoxy-5-fluoro-3'-oxacytidine, also known as 2-hydroxymethyl-5-(5-fluorocytosin-1-yl)-1,3-dioxolane.

As used herein, the term DOC refers to 2'-deoxy-3'-oxacytidine, also known as 2-hydroxymethyl-5-(cytosin-1-yl)-1,3-dioxolane.

As used herein, the term DOT or dioxolane-T refers to 2'-deoxy-3'-oxathymidine, also known as 2-hydroxymethyl-5-(thymidin-1-yl)-1,3-dioxolane.

As used herein, the term "preferential enzyme catalysis" refers to catalysis by an enzyme that favors one substrate over another.

Figure 1:
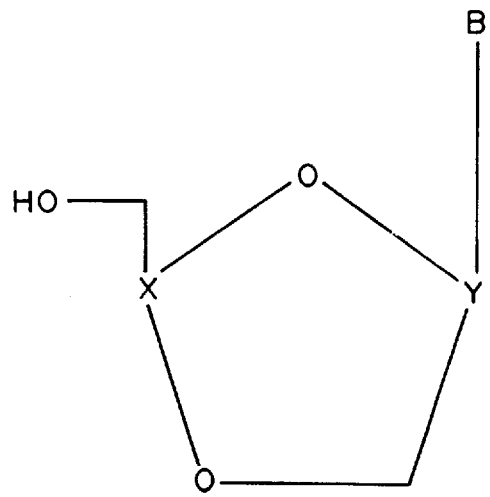
FIG. 1 is an illustration of the chemical structure of a 1,3-dioxolane nucleoside that indicates the position of the two chiral carbon atoms (C1' and C4') in the molecule.

As used herein, the term "1,3-dioxolane nucleoside" refers to a nucleoside in which a purine or pyrimidine base is attached to a 1,3-dioxolane ring through the C5 carbon of the dioxolane (which becomes the C1'-carbon of the nucleoside), as shown in FIG. 1.

As used in this application, the term "predominately" means greater than 80%.

As used herein, the term "protected" means that the functional group, typically an oxygen or nitrogen atom, has been protected by any method known to those skilled in the art for the protection of that group.

As used herein, the term "acylation" means replacement of an H in a functional group of interest with XC(O), wherein X is an alkyl or aromatic group, typically a lower alkyl (C5 or less).

As used herein, the term "alkoxy" refers to an alkyl-O-moiety, wherein the alkyl group can be straight chain, branched, or cyclic.

As used herein, the term "aryloxy" refers to $C_6H_5$—O—, or a derivative thereof in which there is one or more hydrocarbon, halo, or other substituents on the aromatic ring.

As used herein, the term "alkylamino" refers to alkyl-NH—, wherein the alkyl group is straight chain, branched, or cyclic.

As used herein, the term "dialkylamino" refers to (alkyl)$_2$N—, wherein the alkyl group is straight chain, branched, or cyclic.

As used herein, the term "arylamino" refers to $C_6H_5$—NH—, or a derivative thereof in which there is one or more hydrocarbon, halo, or other substituents on the aromatic ring.

As used herein, the term "diarylamino" refers to $(C_6H_5)_2$—N—, or a derivative thereof in which there is one or more hydrocarbon, halo, or other substituents on the aromatic rings.

As used herein the term "alklarylamino" refers to $(C_6H_5)$(alkyl)N—, or a derivative thereof in which there is one or more hydrocarbon, halo, or other substituents on the aromatic ring, and wherein the alkyl group is straight chain, branched, or cyclic.

I. Preparation of Predominately the β-Anomer of 1,3-Dioxolane Nucleosides

A synthesis of 1,3-dioxolane nucleosides is disclosed that includes condensing a 2-O-protected-5-O-acylated-1,3-dioxolane with a purine or pyrimidine base in the presence of a titanium containing Lewis acid of the structure:

$$TiX_nY_{m-n}$$

wherein m=4; n=2, 3, or 4; Ti=titanium; X=Cl, Br, or I; and Y is alkoxy, aryloxy, amino, alkylamino, dialkylamino, arylamino, diarylamino, alkylarylamino, and mixtures thereof, or a bifunctional molecule that contains both an alkoxy and an amino functional group and that is bound to the titanium molecule by both the alkoxy and amino moieties, to provide predominately the desired &isomer in the C1'-position of a 1,3-dioxolane nucleoside.

The process can be used to prepare a wide variety of 1,3-dioxolane nucleosides, including those with a cytosine, thymine, uracil, adenine, or guanine base, and alkylated, halogenated, sulfenylated, and alkoxylated derivatives thereof.

Nonlimiting examples of suitable alkoxy groups that can be present in the titanium catalyst include isopropoxide (Oipr), and other lower alkoxy groups ($C_5$ or less). A nonlimiting example of suitable aryloxy groups include phenoxy. Nonlimiting examples of suitable alkylamine and dialkylamine groups that can be present in the titanium catalyst include those with lower alkyl groups ($C_5$ or less). Examples of suitable arylamino groups that can be present in the titanium catalyst include those with phenyl groups. Examples of bifunctional molecules that contain both an alkoxy and an amino functional group and that can be bound to the titanium molecule by both the alkoxy and amino moieties include 2-aminoethanol, 3-aminopropanol, and 1-substituted and 2-substituted derivatives thereof in which the substituents are lower alkyl ($C_5$ or less) or aryl groups.

The condensation reaction can be carried out under any conditions that provide predominately the β-isomer of the 1,3-dioxolane nucleoside. The reaction is typically carried out in a nonprotic, noncoordinating solvent such as toluene, chloroform, dichloromethane, or carbon tetrachloride, at a temperature typically ranging from −80° C. to room temperature (with elevated temperature used if needed to force the reaction). The reaction is monitored by thin layer chromatography until complete. In certain situations, if the product is allowed to remain in the presence of the Lewis acid for too long, epimerization may occur. The product is purified by conventional methods known to those skilled in the art, including chromatography and recrystallization.

The stereoselectivity of these N-glycosylation reactions can be rationalized on the basis of a preferential heteroatom Lewis acid interaction (Scheme 1, below). Use of Lewis acids (e.g., trimethylsilyl trifluoromethanesulfonate) whose role is solely to generate an oxonium ion, should follow Pathway A and result in no stereocontrol. However, in cases where the Lewis acid can pre-complex to a ring heteroatom (i.e., Pathway B), diastereofacial selectivity can be achieved through the minimization of destabilizing 1,2-steric interactions by complexing anti to the protected hydroxymethyl substituent. At the very least, this complexation should dramatically hinder the approach of the silylated base to the α-face. In addition, an intermediate can be formed wherein the associated metal delivers one of its ligands (presumably chloride) to the α-face of the proximal incipient carbonium ion. The resulting α-chloro derivative can then undergo $S_N2$ attack to form the β-N-glycoside.

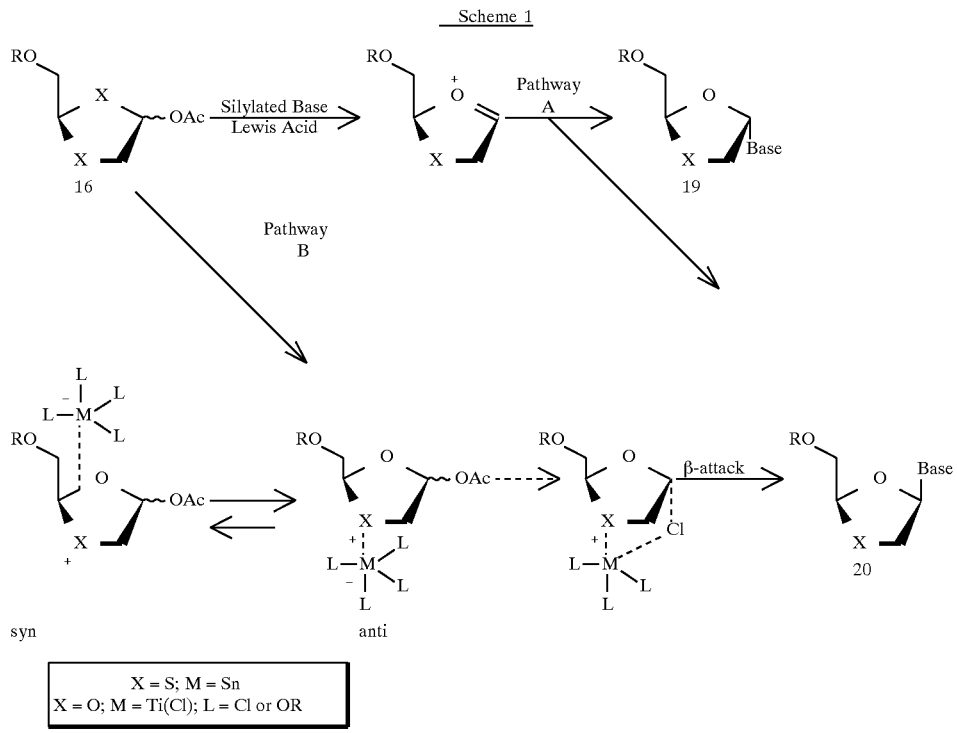

Scheme 1

As examples, β-FDOC, β-DOC and β-DOT can be prepared by coupling a 2-protected hydroxymethyl-4-carboxy-1,3-dioxolane with the appropriate silylated pyrimidine base at ambient temperature using the Lewis acid, $TiCl_4$. Removal of the protecting groups give the free nucleosides β-FDOC, β-DOC, β-DOT or analogues thereof. NMR stereochemical assignments and X-ray structures confirm the β selectivity.

Figure 2:
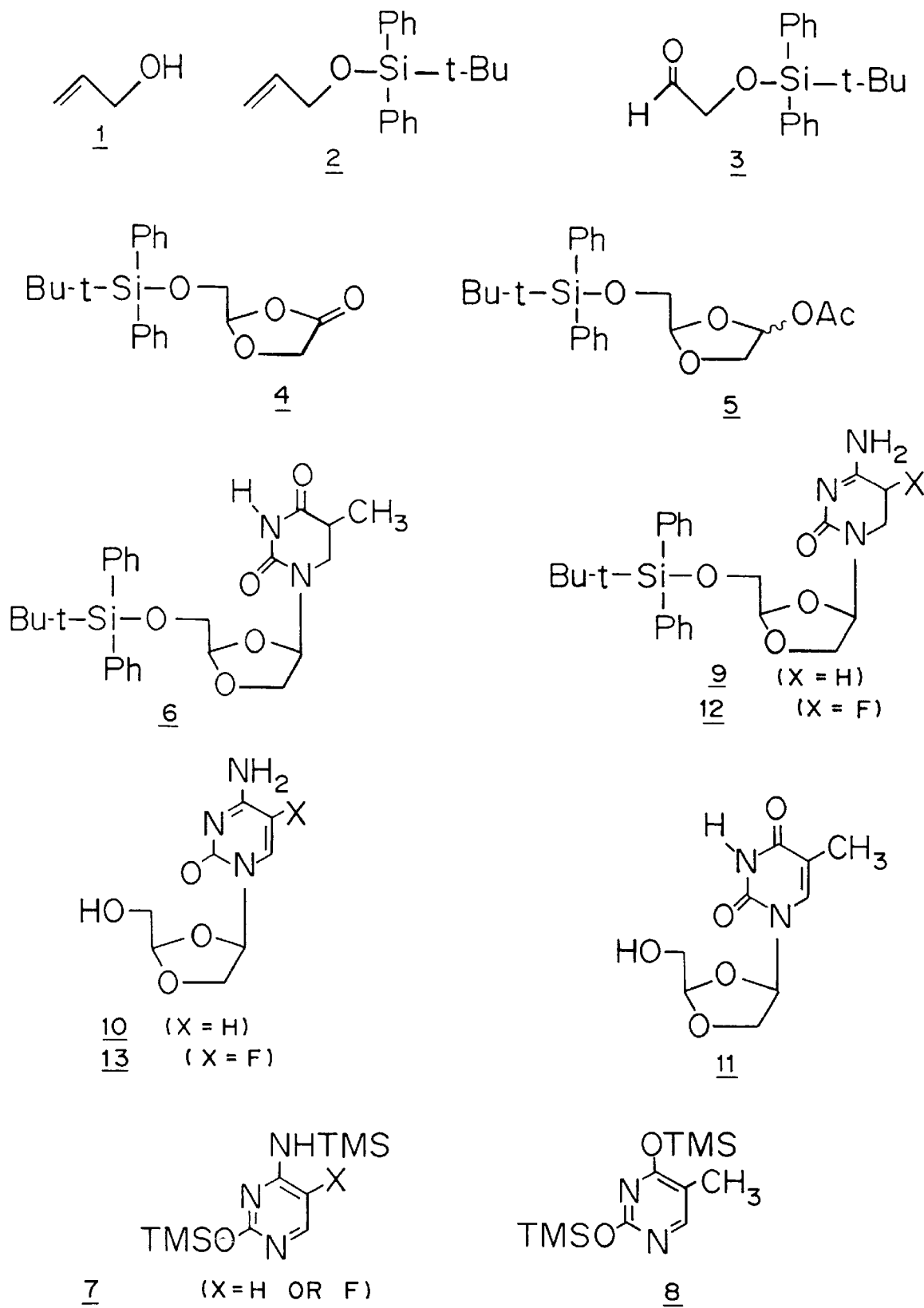
FIG. 2 is an illustration of chemical structures of intermediates used in the reaction scheme for the preparation of 2'-deoxy-3'-oxa-cytidine (DOC, compound 10), 3'-deoxy-3'-oxa-thymidine (DOT, compound 11), and 2'-deoxy-5-fluoro-3'-oxa-cytidine (FDOC, compound 13).

FIG. 2 is an illustration of chemical structures of intermediates used in the reaction scheme set out in detail below for the preparation of 2'-deoxy-3'-oxa-cytidine (DOC, compound 10), 3'-deoxy-3'-oxa-thymidine (DOT, compound 11), and 2'-deoxy-5-fluoro-3'-oxa-cytidine (FDOC, compound 13).

The 1,3-dioxolane ring can be prepared by known methods. In one method, an allyl ether or ester 1 is ozonized (see FIG. 2) to give an aldehyde 3, which reacts with glycolic acid to give a lactone 4. The lactone 4 is treated with a reducing agent such as DIBAL (diisobutylaluminum chloride), Red Al (bis(2-methoxyethyoxy)aluminum hydride), and LiAl(O-t-butyl)$_3$H. followed by a carboxylic anhydride, to produce the carboxylate 5. This carboxylate is coupled with a silylated pyriridine base 8 or a silylated 5-fluoro substituted pyrimidine base 7 in the presence of a titanium containing Lewis acid that can catalyze stereoselective coupling, including $TiCl_4$, $TiCl_3(OiPr)$ or $TiCl_2(OiPr)_2$, wherein OiPr refers to isopropoxide, to yield the β-isomer of the nucleoside 9 or substituted nucleoside 12 in a high ratio of β:α isomers. The nucleoside 9 or substituted nucleoside 12 is deprotected to produce 10 or 13 or modified at the 5'-position to form a 1,3-dioxolane prodrug analogue.

The term "silylated pyrimidine or purine base", as used herein, refers to a pyrimidine or purine wherein the functional oxygen and nitrogen groups have been protected with suitable silyl moieties. Silyl protecting groups are known to those skilled in the art, and include trialkylsilyl groups of the formula $-S_1(R_1)(R_2)(R_3)$ wherein $R_1$, $R_2$, and $R_3$ are lower-alkyl, e.g., methyl, ethyl, butyl, and alkyl possessing S carbon atoms or less, or phenyl. Furthermore, $R_1$ can be identical to $R_2$, and $R_1$, $R_2$, and $R_3$ can all be identical. Examples of trialkylsilyl groups include, but are not limited to, trimethylsilyl and t-butyldiphenylsilyl.

As used herein, a leaving group means a functional group that forms an incipient carbocation when it leaves.

Illustrative examples of the synthesis of dioxolane nucleosides according to the present invention are given in Example 1 below.

EXAMPLE 1

Synthesis of Dioxolane Nucleosides

FIG. 2 illustrates the synthesis of 2'-deoxy-3'-oxacytidine (DOC), 2'-deoxy-3'-oxathymidine (DOT), and 2'-deoxy-5-fluoro-3'-oxacytidine (FDOC).

The synthesis of the 1,3-dioxolane moiety begins with allyl alcohol 1. A NaH oil suspension (4.5 g, 60%, 110 mmol) was washed with THF twice (100 ml×2) and the resulting solid suspended in the THF (300 ml). The suspension was cooled to 0° C., allyl alcohol 1 (6.8 ml, 100 mmol) was added dropwise, and the mixture was stirred for 30 minutes at 0° C. t-Butyldiphenylsilyl chloride (25.8 ml, 100.8 mmol) was added dropwise at 0° C. and the reaction mixture was stirred for 1 hour at 0° C. The solution was quenched with water (100 ml), and extracted with diethyl ether (200 ml×2). The combined extracts were washed with water, dried over $MgSO_4$, filtered, concentrated, and the residue distilled under vacuum (90°–100° C. at 0.5–0.6 mm Hg) to give a colorless liquid 2 (28 g., 94 mmol, 94%). ($^1$H NMR: ($CDCl_3$, 300 MHz) 7.70–7.35 (10H, m, aromatic-H); 5.93 (1H, m, $H_2$); 5.37 (1H, dt, $H_1$) J=1.4 and 14.4 Hz; 5.07 (1H, dt, $H_1$) J=1.4 and 8.7 Hz; 4.21 (2H, m, $H_3$); 1.07 (9H, s, t-Bu)).

The silyl allyl ether 2 (15.5 g, 52.3 mmol) was dissolved in $CH_2Cl_2$ (400 ml), and ozonized at −78° C. Upon completion of ozonolysis, DMS (15 ml, 204 mmol, 3.9 eq) was added at −78° C. and the mixture was warmed to room temperature and stirred overnight. The solution was washed with water (100 ml×2), dried over $MgSO_4$, filtered, concentrated, and distilled under vacuum (100°–110° C. at 0.5–0.6 mm Hg) to give a colorless liquid, a silylated glycoaldehyde 3 ((15.0 g, 50.3 mmol, 96%). ($^1$H NMR: ($CDCl_3$, 300 MHz) 9.74 l1H, s, H—CO); 7.70–7.35 (10H, m, aromatic-H); 4.21 (2H, s, —$CH_2$); 1.22 (9H, s, t-Bu)).

Alternative route to Compound 3 bis-t-Butyldiphenylsilyl ether of cis-2-butene-1,3-diol

NaH oil suspension (4.5 g, 60%, 110 mmol) was washed with THF twice (100 ml×2) and the resulting solid suspended in THF (300 ml). The suspension was cooled to 0° C., and to it was added allyl alcohol (6.8 ml, 100 mmol) dropwise, and the mixture was stirred for 0.5 h at 0° C. t-Butyldiphenylsilyl chloride (25.8 ml, 100.8 mmol) was added dropwise at 0° C., and the reaction mixture stirred for 1 h at 0° C. The solution was quenched with water (100 ml), and extracted with $ET_2O$ (200 ml×2). The combined extracts were washed with water, dried over $MgSO_4$, filtered, concentrated, and the residue was distilled under vacuum (90°–100° C. at 0.5–0.6 mm Hg) to give a colorless liquid bis-t-butyldiphenylsilyl ether of cis-2-butene-1,3-diol (28 g, 94 mmol, 94%). $^1$H NMR: ($CDCl_3$, 300 MHz) 7.70–7.35 (10H, m, aromatic H), 5.93 (1H, m, $H_2$), 5.37 (1H, dt, $H_1$, J=14.4 Hz), 5.07 (1H, dt, $H_1$, J=1.4 and 8.7 Hz), 4.21 (2 H, m, $H_3$), 1.07 (9H,s,t-Bu).

Ozonolysis of bis-t-Butyldiphenylsilyl ether of cis-2-butene-1,3-diol. bis-t-Butyldiphenysilyl ether of cis-2-butene-1,3-diol (15.5 g, 52.3 mmol) was dissolved in $CH_2Cl_2$ (400 ml), and ozonized at −78° C. Upon completion of ozonolysis, dimethyl sulfide (15 ml, 204 mmol, 3.9 eq) was added at −78° C., and the mixture was warmed to room temperature and stirred overnight. The solution was washed with water (100 ml×2), dried over $MgSO_4$, filtered, concentrated, and distilled under vacuum (100°–110° C. at 0.5–0.6 mm Hg) to give a colorless liquid aldehyde (15.0 g, 50.3 mmol, 96%).

$^1$H NMR: ($CDCl_3$, 300 MHz) 9.74 (1H, s, H—CO), 7.70–7.35 (10H, m, aromatic H), 4.21 (2H, s, —$CH_2$), 1.22 (9H, s, t-Bu); IR (Neat) 3080, 3060, 2970, 2940, 2900, 2870, 1730, 1470, 1460, 1430, 1390, 1360, 1310, 1200, 1110, 1030, 960, 880, 830, 745, 710.

A portion of the silylated glycoaldehyde 3 (4.0 g, 13.40 mmol) was dissolved in 1,2-dichloroethane (50 ml) and to it was added glycolic acid (1.10 g, 14.46 mmol) in one portion and p-toluenesulfonic acid (0.1 g). The mixture was refluxed for 1 hour. The volume of the solution was then reduced to about half by distilling off the solvent with a Dean-Stark trap. Another 50 ml of dichloroethane was added and the solution refluxed for 30 minutes again. The solution was cooled to room temperature and concentrated under vacuum. The residue was dissolved in ether (200 ml) and the solution washed with $NaHCO_3$ solution (50 ml) and water (50 ml). The combined extracts were dried over $MgSO_4$, filtered, and concentrated to give a colorless oil which gradually solidified under vacuum. Recrystalliaation from hexane afforded a waxy white solid 4 (2-(t-Butyl-diphenylsilyloxy)-methyl-4-oxo-1,3-dioxolane) (4.2 g, 11.78 mmol, 88%). ($^1$H NMR: ($CDCl_3$, 300 MHz) 7.66 & 7.42 (10H, m, aromatic-H), 5.72 (1H, broad, $H_2$), 4.46 (1H, d, 1$H_5$, J=14.4 Hz), 4.28 (1H, d, 1$H_5$, J=14.4 Hz), 3.81 (2H, d, 2$CH_2O$, J=1.8 Hz), 1.04 (9H, s, t-Bu); mp 94°–95° C.; MS (FAB) 357 (M+H), 299, 241, 197, 163, 135, 91; Anal. Calc'd for $C_{20}H_{24}O_4Si$: C, 67.38; H, 6.79; Found: C, 67.32; H, 6.77).

4-Acetoxy-2-(t-Butyldiphenylsilyloxymethyl)-1,3-dioxolane 29 was prepared using either of the following procedures A or B.

Procedure A: (DIBAL-H) The lactone 4 (1.0 g, 2.81 mmol) was dissolved in toluene (100 ml), and the solution cooled to −78° C. Dibal-H solution (3.0 ml, 1.0M in hexanes, 3 mmol) was added dropwise, while the inside temperature was kept below −70° C. throughout the addition. After the addition was completed, the mixture was stirred for 0.5 hours at −78° C. To it was added $Ac_2O$ (5 ml, 53 mmol) and the mixture, with continuous stirring, was allowed to reach room temperature overnight. Water (5 ml) was added to it and the mixture was stirred for 1 hour, $MgSO_4$ (40 g) was then added, and the mixture was stirred vigorously for 1 hour at room temperature. The mixture was filtered, concentrated, and the residue flash chromatographed with 20% EtOAc in hexanes to give a colorless liquid 5 (0.70 g) which was a mixture of the desired acetates and the aldehyde 3 derived from the ring opening reaction.

Procedure B: (LiAlH(OtBu)$_3$) Lactone 4 (451.5 mg, 1.27 mmoles) was dissolved in 6 ml THF (dry), and cooled to −5° C. To this was added 1.7 ml (1.7 mmoles) of a LiAl(OtBu)$_3$H solution (1M in THF; Aldrich) over a 45 minute period. After addition was completed, the mixture was stirred for 7½ hrs. at 0° C. After this time, 1.2 ml (13 mmoles, 10 eq) of dry acetic anhydride was added, followed by 78 mg (0.64 mmoles, 0.5 equiv.) of DMAP (4-dimethylaminopyridine). The reaction was kept at 0° C. for 14 hours, and the quenched at 0° C. by adding 1 ml NaHCO$_3$ and 0.5 g of Na2CO$_3$. The mixture was stirred for 1 hour at 0° C., and then filtered over a 2 inch plug of silica gel (with 6/1-Hexanes/EtOAc), followed by solvent removal to give 930 mg of a yellow oil (1:1.2 ratio at the glycosidic center). Column chromatography (Hexanes/EtOAc, 6/1) gave 332.9 mg of the acetate, which was 90% pure by $^1$H NMR (299.6 mg, 59% yield).

($^1$H NMR: (CDCl$_3$, 300 MHz) 1.02 (s, 9H, major isomer), 1.04 (s, 9H, minor isomer), 1.96 (s, 3H, minor), 2.12 (s, 3H, major), 3.7 (m, 2H), 4.07 (m, 2H), 5.24 (t, 1H, minor, J=4.2 Hz), 5.37 (t, 1H, major, J=3 Hz), 6.3 (t, 1H, minor, J=3.9 Hz), 6.37 (dd, 1H, major, J=1.5 Hz, J=4.5 Hz), 7.39 (m, 6H), 6.67 (m, 4H). IR (neat): cm$^{-1}$ 3090, 2980, 2880, 1760, 1475, 1435, 1375, 1240, 1120, 1000. MS (FAB. Li$^+$): 407(M+Li), 312, 282, 241, 197, 162, 125. Anal. Calc. for C$_{22}$H$_{28}$O$_5$Si: C, 65.97%, H, 7.05%; Found: C, 66.60%, H, 7.27%).

The crude acetate 5 (0.25 g, 0.62 mmol, quantity assumed with 0.50 g of the previous mixture) was dissolved in methylene chloride (50 ml), and to it the silylated cytosine 7 (X=H) (0.10 g, 0.63 mmol) was added in one portion. The mixture was stirred for 10 minutes, and to it a TiCl$_4$ solution (1.30 ml, 1.0M solution in CH$_2$Cl$_2$, 1.30 mmol) was added, dropwise, at room temperature. It took 2 hours to complete the reaction. Upon completion, the solution was concentrated, the residue was triturated with pyridine (2 ml) and subjected to flash chromatography (first with neat EtOAc then 20% ETOH in EtOAc) to give a tan solid, which was further recrystallized to give a white crystalline solid 9 (0.25 g, 0.55 mmol, 89%). ($^1$H NMR (CDCl$_3$, 300 MHz) 7.97 (1H, d, H$_6$, J=7.8 Hz), 7.67 & 7.40 (10H, m, aromatic-H), 6.24 (1H, d, H$_{1'}$), 5.62 (1H, d, H, J=7.6 Hz), 5.03 (1H, t, H$_{4'}$), 4.20 (1H, dd, 1H$_{2'}$, J=1.2 and 9.0 Hz), 4.15 (1H, dd, 1H$_{2'}$, J=4.8 & 9.0 Hz), 3.96 (1H, dd, 1H$_{5'}$, J=2.1 and 8.7 Hz), 3.93 (1H, dd, 1H$_{5'}$, J=2.1 and 8.7 Hz), 1.08 (9H, s, t-Bu).)

Silylether 9 (0.12 g, 0.27 mmol) was dissolved in THF (20 ml), and an n-Bu$_4$NF solution (0.30 ml, 1.0M solution in THF, 0.30 mmol) was added, dropwise, at room temperature. The mixture was stirred for 1 hour and concentrated under vacuum. The residue was taken up with EtOH/pyridine (2 ml/2 ml), and subjected to flash chromatography (first with EtOAc, then 20% ETOH in EtOAc) to afford a white solid, which was further recrystallized from ETOH to give a white crystalline solid 33 (DOC) (55 mg, 0.26 mmol, 96%). ($^1$H NMR: (DMSO-d$^6$, 300 MHz) 7.79 (1H, d, H$_6$, J=7.5 Hz), 7.18 and 7.11 (2H, broad, NH), 6.16 (1H, dd, H$_{1'}$, J=3.0 & 4.2 Hz), 5.70 (1H, d, H$_5$, J=7.5 Hz), 5.16 (1H, t, OH, J=6.0 Hz), 4.91 (1H, t, H$_{4'}$, J=2.7 Hz), 4.05 (2H, m, H$_{2'}$), 3.62 (2H, m, 2H$_{5'}$); mp 183°–184° C.

The coupling reaction of acetate 5 with silylated thymine 8 showed a titanium species dependent selectivity in accordance with the following observations (ratios were determined by $^1$H NMR of the crude reaction mixtures):

| Titanium Species | β:α Ratio |
|---|---|
| TiCl$_4$ | 7:1 |
| TiCl$_3$(OiPr) | 10.1 |
| TiCl$_2$(OiPr)$_2$ | >98:2 |

In the coupling reaction using TiCl$_3$(OiPr), the impure acetate 5 from the procedure B reduction above (assumed 69% of the mixture, 185.4 mg, 0.4653 mmol) was dissolved in 8 ml of dry dichloromethane along with 144 mg (1.15 eq) of silylated thymine 8, and this mixture was stirred under argon at room temperature. Next 0.57 ml (1.15 eq) of a freshly prepared solution of TiCl$_3$(OiPr) in dichloromethane (1M solution prepared from 2 eq of TiCl$_4$ and 1 eq of TiCl(OiPr)$_3$) was added dropwise over a 25 minute period. After 2.5 hours, 0.07 ml (0.15 eq) of a TiCl$_4$/dichloromethane solution (1M, Aldrich Chemical Company, Milwaukee, Wis.) was added and the reaction was stirred for an additional hour. Then 3 ml of ethanol and 5 ml of NaHCO$_3$ solution were added, stirred for 10 minutes, followed by extraction with additional NaHCO$_3$ solution. The aqueous layer was separated, washed twice with 100 ml of dichloromethane, and the organic layers were combined and dried over MgSO$_4$. Filtration, solvent removal, column chromatography (1/2: Hexanes/EtOAc), and then recrystallization (1/1: Hexanes/Et$_2$O) gave 160 mg (74%) of compound 6 as a white powder. ($^1$H NMR: (CDCl$_3$, 300 MHz) 1.06 (s, 9H), 1.68 (s, 3H), 3.91 (t, 2H, J=3.3 Hz), 4.14 (d, 2H, J=3.9 Hz), 5.06 (t, 1H, J=3.3 Hz), 6.34 (t, 1H, J=3.9 Hz), 7.4 (m, 6H), 7.7 (m, 4H), 8.62 (bs, 1H). MS (FAB. Li$^+$): 473 (M+Li), 409, 307, 241, 197, 154, 127. Anal. Calc. for C$_{25}$H$_{30}$O$_5$N$_2$Si: C, 64.35%; H, 6.48%; N, 6.00%; Found: C, 64.42%; H, 6.52%; N, 5.97%.

Alternative Procedure 1.156 g (70% by $^1$H NMR, 0.809 g, 2.02 mmoles) of the acetate from Procedure B was dissolved in 25 ml of CH$_2$Cl$_2$ with 640 mg (1.15 equiv.) of silylated fluorocytosine. Next, 2.222 mmoles of TiCl$_3$(OiPr) was added as a solution with 6 ml CH$_2$Cl$_2$ (see previous experimental for TiCl$_3$(OiPr) preparation), over a 70 minute period. After 2 hours total time, 1.1 ml of TiCl$_4$/CH$_2$Cl$_2$ (1 ml solution, Aldrich, 0.55 equiv.) was added over 45 minutes. This mixture was then stirred for 16 hours, and then an additional 0.3 ml. of TiCL$_4$/CH$_2$Cl$_4$ was added with stirring for 2 more hours. The mixture was then sequentially quenched with 20 ml of hours. The mixture for 30 minutes, followed by filtration over 2 inches of silica gel with 6/1-EtOAc/EtOH, followed by solvent removal gave 1.28 g of a yellowish form (9:1 β:α by $^1$H NMR). Column Chromatography (6/1-EtOAc/EtOH) gave 490 mg (52% yield) of the coupled product as a white powder.

In the coupling reaction using TiCl$_2$(OiPr)$_2$, impure acetate from the procedure B reduction (assumed 50% of the mixture, 444 mg, 1.11 mmol) was dissolved in 18 ml of dry dichloromethane along with 654.1 mg of silylated thymine 8 and stirred at room temperature under argon. Next, 1.3 ml of a 2M TiCl$_2$(OiPr)$_2$/CH$_2$/Cl$_2$ solution was added over a 20 minute period. After 14 hours, 1 ml of a 1M TiCl$_4$/CH$_2$Cl$_2$ solution was added and the reaction was stirred for an additional 3 hours. Then 4 ml of concentrated NH$_4$OH was added, along with 10 ml of dichloromethane. Ten minutes of stirring followed by filtration over 1 inch of silica gel with EtOAc, solvent removal and then column chromatography of the resulting oil gave 164.9 mg (32%) of compound 10.

The silyl ether 6 (60.9 mg, 0.131 mmol) was dissolved in 2 ml of THF and 0.14 ml of a Bu$_4$NF/THF solution (1M, Aldrich was added. After stirring for 24 hours, the solvent was removed in a vacuum and column chromatography (5/1: EtOAc/EtOH) of the resulting oil gave 22.6 mg (76%) of the desired nucleoside 11 (DOT) as a white powder. ($^1$H NMR: (HOD (4.8 ppm),, 300 MHz) 1.83 (s, 3H), 3.82 (m, 2H), 4.18 (dd, 1H, J=10.5 Hz, J=6 Hz), 5.06 (s, 1H), 6.33 (d, 1H, J=5.7 Hz), 7.72 (s, 1H).

The impure acetate 5 from the procedure B reduction above (assumed 80% by $^1$H NMR analysis, 117.6 mg, 0.294 mmol) and 120.8 mg (1.5 eq) of silylated fluorocytosine 7 (X=F) were dissolved in 10 ml of dry dichloromethane. Then 0.59 ml (2 eq) of a $TiCl_4$/dichloromethane solution was added dropwise over 1 hour. After stirring for 30 additional minutes, 5 ml of dichloromethane and 1 ml of concentrated $NH_4OH$ were added, the solvent was removed in a vacuum, and column chromatography (EtOAc/EtOH: 1/1) gave 35 mg (25%) of compound 12 as a white solid. ($^1$H NMR ($CDCl_3$, 300 MHz) 1.06 (s, 9H), 3.62 (dq, 2H, J=2.7 Hz, J=12.3 Hz), 3.9 (m, 2H), 5.01 (t, 1H, J=2.4 Hz), 6.2 (m, 1H), 7.41 (m, 6H), 7.7 (m, 4H), 7.92 (d, 1H, J=6 Hz).)

The silyl ether 12 (116.8 MG, 0.249 mmol) was dissolved in 3 ml of dry THF, and 0.3 ml of a $Bu_4NF$/THF solution (1M, Aldrich Chemical Company, Milwaukee, Wis.) was added. After 3 hours of stirring, the solvent was removed by vacuum, and column chromatography (EtOAc/EtOH: 4/1) gave 48.1 mg (84%) of the nucleoside 13 (FDOC) as a white powder. ($^1$H NMR: (DMSO-$d^6$, 300 MHz) 3.63 (m, 2H), 4.01 (dd, 1H, J=5.1 Hz, J=9.6 Hz), 4.08 (d, 1H, J=9.6 Hz), 4.87 (s, 1H), 5.26 (t, 1H, J=6 Hz), 6.07 (m, 1H), 7.49 (bs, 1H), 7.73 (bs, 1H), 8.12 (d, 1H, J=7.2 Hz).)

II. Process for the Resolution of C4'-Racemic Mixtures of 1,3-Dioxolane Nucleosides A method is provided for the resolution of racemic mixtures of C4'-nucleoside enantiomers of 1,3-dioxolane nucleosides. The method involves the use of enzymes for which one enantiomer is a substrate and the other enantiomer is not. The enzyme catalyses the reaction in the "recognized" enantiomer, and then the reacted enantiomer is separated from the unreacted enantiomer on the basis of the new difference in physical structure. Given the disclosure herein, one of skill in the art will be able to choose an enzyme that is selective for the nucleoside enantiomer of choice (or selective for the undesired enantiomer, as a method of eliminating it), by selecting of one of the enzymes discussed below or by systematic evaluation of other known enzymes. Given this disclosure, one of skill in the art will also know how to modify the substrate as necessary to attain the desired resolution. Through the use of either chiral NMR shift reagents or polmimetry, the optical enrichment of the recovered ester can be determined.

The following examples further illustrate the use of enzymes to resolve racemic mixtures of enantiomers. Other known methods of resolution of racemic mixtures can be used in combination with the method of resolution disclosed herein. All of these modifications are considered within the scope of the invention. The following examples are not intended to limit the scope of the invention.

Resolution Based on Hydrolysis of C5'-Nucleoside Esters

In one embodiment, the method includes reacting the C5'-hydroxyl group of a mixture of 1,3-dioxolane nucleoside racemates with an acyl compound to form C5'-esters in which the nucleoside is in the "carbinol" end of the ester. The racemic mixture of nucleoside C5'-esters is then treated with an enzyme that preferentially cleaves, or hydrolyses, one of the enantiomers and not the other.

An advantage of this method is that it can be used to resolve a wide variety of nucleosides, including pyrimidine and purine nucleosides that are optionally substituted in the carbohydrate moiety or base moiety. The broad applicability of this method resides in part on the fact that although the carbinol portion of the ester plays a role in the ability of an enzyme to differentiate enantiomers, the major recognition site for these enzymes is in the carboxylic acid portion of the ester. Further, one may be able to successfully extrapolate the results of one enzyme/substrate study to another, seemingly-different system, provided that the carboxylic acid portions of the two substrates are the same or substantially similar.

Another advantage of this method is that it is regioselective. Enzymes that hydrolyse esters typically do not catalyze extraneous reactions in other portions of the molecule. For example, the enzyme lipase catalyses the hydrolysis of the ester of 2-hydroxymethyl-5-oxo-1,3-oxathiolane without hydrolysing the internal lactone. This contrasts markedly with "chemical" approaches to ester hydrolysis.

Still another advantage of this method is that the separation of the unhydrolysed enantiomer and the hydrolysed enantiomer from the reaction mixture is quite simple. The unhydrolysed enantiomer is more lipophilic than the hydrolysed enantiomer and can be efficiently recovered by simple extraction with one of a wide variety of nonpolar organic solvents or solvent mixtures, including hexane and hexane/ether. The less lipophilic, more polar hydrolysed enantiomer can then be obtained by extraction with a more polar organic solvent, for example, ethyl acetate, or by lyophilization, followed by extraction with ethanol or methanol. Alcohol should be avoided during the hydrolysis because it can denature enzymes under certain conditions.

Enzymes and Substrates

With the proper matching of enzyme and substrate, conditions can be established for the isolation of either nucleoside enantiomer. The desired enantiomer can be isolated by treatment of the racemic mixture with an enzyme that hydrolyses the desired enantiomer (followed by extraction of the polar hydrolysate with a polar solvent) or by treatment with an enzyme that hydrolyses the undesired enantiomer (followed by removal of the undesired enantiomer with a nonpolar solvent).

Enzymes that catalyze the hydrolysis of esters include esterases, for example pig liver esterase, lipases, including porcine pancreatic lipase and Amano PS-800 lipase, substillisin, and α-chymotrypsin.

The most effective acyl group to be used to esterify the C5'-position of the nucleoside can be determined without undue experimentation by evaluation of a number of homologs using the selected enzyme system. For example, when 1,3-oxathiolane nucleosides are esterified with butyric acid, resolutions with both pig liver esterase and Amano PS-800 proceed with high enantioselectivity (94–100 enantiomeric excess) and opposite selectivity. Non-limiting examples of other acyl groups that can be evaluated for use with a particular nucleoside enantiomeric mixture and particular enzyme include alkyl carboxylic acids and substituted alkyl carboxylic acids, including acetic acid, propionic acid, butyric acid, and pentanoic acid. With certain enzymes, it may be preferred to use an acyl compound that is significantly electron-withdrawing to facilitate hydrolysis by weakening the ester bond. Examples of electron-withdrawing acyl groups include α-haloesters such as 2-chloropropionic acid, 2-chlorobutyric acid, and 2-chloropentanoic acid. α-Haloesters are excellent substrates for lipases.

Resolution Conditions

The enzymatic hydrolyses are typically carried out with a catalytic amount of the enzyme in an aqueous buffer that has a pH that is close to the optimum pH for the enzyme in question. As the reaction proceeds, the pH drops as a result of liberated carboxylic acid. Aqueous base should be added to maintain the pH near the optimum value for the enzyme. The progress of the reaction can be easily determined by monitoring the change in pH and the amount of base needed to maintain pH. The hydrophobic ester (the unhydrolysed enantiomer) and the more polar alcohol (the hydrolysed enantiomer) can be sequentially and selectively extracted from the solution by the judicious choice of organic solvents. Alternatively, the material to be resolved can be passed through a column that contains the enzyme immobilized on a solid support.

Enzymatic hydrolyses performed under heterogeneous conditions can suffer from poor reproducibility. Therefore, it is preferred that the hydrolysis be performed under homogeneous conditions. Alcohol solvents are not preferred because they can denature the enzymes. Cosolvents that do not denature enzymes should be used, such as acetonitrile. Homogeneity can be achieved through the use of non-ionic surfactants, such as Triton X-100. However, addition of these surfactants not only assists in dissolving the starting material, they also enhances the aqueous solubility of the product. Therefore, although the enzymatic reaction can proceed more effectively with the addition of a non-ionic surfactant than under heterogeneous conditions, the isolation of both the recovered staring material and the product can be made more difficult. The product can be isolated with appropriate chromatographic and chemical (e.g., selective salt formation) techniques. Diacylated nucleosides can be used but are often quite lipophilic and hard to dissolve in the medium used.

B. Therapeutic Use of 1.3-Dioxolane Nucleosides

A number of compounds made according to this invention either possess antiretroviral activity, such as anti-HIV-1, anti-HIV-2 and anti-simian immunodeficiency virus (anti-SIV) activity, themselves and/or are metabolizable to species that possess antiretroviral activity. Thus, these compounds, pharmaceutically acceptable derivatives or salts of these compounds or pharmaceutically acceptable formulations containing these compounds or their derivatives are useful in the prevention and treatment of viral infections in a host such as a human, preferably HIV infections and other AIDS-related conditions such as AIDS-related complex (ARC), persistent generalized lymphadenopathy (PGL), AIDS-related neurological conditions, anti-HIV antibody positive and HIV-positive conditions, Kaposi's sarcoma, thrombocytopenia purpurea and opportunistic infections. In addition, these compounds or formulations can be used prophylactically to prevent or retard the progression of clinical illness in individuals who are anti-HIV antibody or HIV-antigen positive or who have been exposed to HIV.

Thus, humans can be treated by administering to the patient a pharmaceutically effective amount of the active nucleoside prodrug analogues in the presence of a pharmaceutically acceptable carrier or diluent such as a liposomal suspension. A preferred carrier for oral administration is water, especially sterilized water. If administered intravenously, the preferred carriers are physiological saline or phosphate buffered saline. The compounds according to the present invention are included in the pharmaceutically acceptable carrier in an amount sufficient to exert a therapeutically useful inhibitory effect on HIV in vivo without exhibiting adverse toxic effects on the patient treated. Pharmaceutically compatible binding agents and/or adjuvant materials may also be included as part of the composition. The active materials can also be mixed with other active materials that do not impair the desired action and/or supplement the desired action.

It will be appreciated by those skilled in the art that the effective amount of a compound or formulation containing the compound required to treat an individual will vary depending on a number of factors, including whether the compound or a prodrug analogue is administered, the route of administration, the nature of the condition being treated and the age and condition of the patient. In general, however, an effective dose for all of the above-described conditions, will range from about 1–50 mg per kg body weight of the patient per day, preferably 1–20 mg/kg/day, and more generally, 0.1 to 100 mg per kilogram per day. Preferably, a dose will produce peak blood levels of the active compound that range from about, 0.2 to 70 uM, preferably 1–10 $\mu$M, and most preferably about 5 $\mu$M. The desired dose may be given in a single dose or as divided doses administered at appropriate intervals, such as two, three, four or more sub-doses per day.

Thus, the active compounds, or derivatives or salts thereof, or formulations containing these compounds or their pharmaceutically acceptable derivatives or salts, can be conveniently administered by any convenient route of administration, such as parenteral, including intramuscular, subcutaneous and intravenous; oral; rectal; nasal; vaginal or by inhalation. The compounds can be administered in unit dosage form for all of the above-identified conditions, such as formulations containing 7 to 3000 mg, perferably 70 to 1400 mg, and most preferably, 1 to 10 mg of active ingredient per unit dosage form.

A preferred made of administration of the compounds of this invention is oral. Oral compositions will generally include an inert diluent or an edible carrier. They may be enclosed in gelatin capsules or compressed into tablets. For the purpose of oral therapeutic administration, the compounds of this invention may be incorporated with excipients and used in the form of tablets, troches, capsules, elixirs, suspensions, syrups, wafers, chewing gums and the like. An oral dosage of 50–1000 mg is usually convenient.

The active compound can be administered as any derivative that upon administration to the recipient, is capable of providing directly or indirectly, the parent compound, or that exhibits activity itself. Nonlimiting examples are the pharmaceutically acceptable salts (alternatively referred to as "physiologically acceptable salts"), and the 5' and $N^4$ acylated or alkylated derivatives of the active compound (alternatively referred to as "physiologically active derivatives"). In one embodiment, the acyl group is a carboxylic acid ester in which the non-carbonyl moiety of the ester group is selected from straight, branched, or cyclic alkyl, alkoxyalkyl including methoxymethyl, aralkyl including benzyl, aryloxyalkyl such as phenoxymethyl, aryl including phenyl optionally substituted with halogen, $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxytrityl, substituted benzyl, trialkylsilyl (e.g. dimethyl-t-butylsilyl) or diphenylmethylsilyl. Aryl groups in the esters optimally comprise a phenyl group. The alkyl group can be straight, branched, or cyclic, and is optimally a $C_1$ to $C_{18}$ group.

Specific examples of pharmaceutically acceptable derivatives include, but are not limited to:

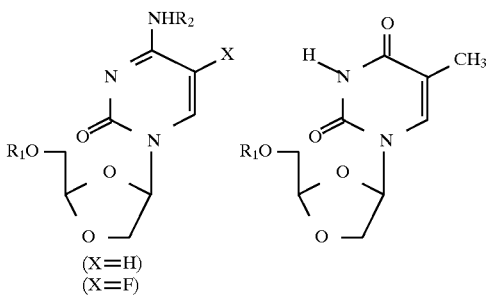

(X=H)
(X=F)

wherein $R_1$ and $R_2$ are independently selected from the group consisting of alkyl and acyl, specifically including but not limited to methyl, ethyl, propyl, butyl, pentyl, hexyl, isopropyl, isobutyl, sec-butyl, t-butyl, isopentyl, amyl, t-pentyl, 3-methylbutyryl, hydrogen succinate, 3-chlorobenzoate, cyclopentyl, cyclohexyl, benzoyl, acetyl, pivaloyl, mesylate, propionyl, butyryl, valeryl, caproic, caprylic, capric, lauric, myristic, palmitic, stearic, oleic, amino acids including but not limited to alanyl, valinyl, leucinyl, isoleucinyl, prolinyl, phenylalaninyl, tryptophanyl, methioninyl, glycinyl, serinyl, threoninyl, cysteinyl, tyrosinyl, asparaginyl, glutaminyl, aspartoyl, glutaoyl, lysinyl, argininyl, and histidinyl, and wherein one of $R_1$ and $R_2$ can be H.

Derivatives can be provided in the form of pharmaceutically acceptable salts. As used herein, the term pharmaceutically acceptable salts or complexes refers to salts or complexes that retain the desired biological activity of the parent compound and exhibit minimal, if any, undesired toxicological effects. Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acids, naphthalenedisulfonic acids, and polygalacturonic acid; (b) base addition salts formed with polyvalent metal cations such as zinc, calcium, bismuth, barium, magnesium, aluminum, copper, cobalt, nickel, cadmium, sodium, potassium, and the like, or with an organic cation formed from N,N-dibenzylethylene-diamine, ammonium, or ethylenediamine; or (c) combinations of (a) and (b); e.g., a zinc tannate salt or the like.

Modifications of the active compound, specifically at the $N^4$ and 5'-0 positions, can affect the bioavailability and rate of metabolism of the active species, thus providing control over the delivery of the active species. Further, the modifications can affect the antiviral activity of the compound, in some cases increasing the activity over the parent compound. This can easily be assessed by preparing the derivative and testing its antiviral activity according to the methods described herein, or other method known to those skilled in the art.

Methodology for Testing Antiviral Activity

Antiviral compositions can be screened in vitro for inhibition of HIV by various experimental techniques. one such technique involves measuring the inhibition of viral replication in human peripheral blood mononuclear (PBM) cells. The amount of virus produced is determined by measuring the quantity of virus coded reverse transcriptase (RT), an enzyme found in retroviruses, that is present in the cell culture medium.

PBM cells from healthy HIV-1 and hepatitis B virus seronegative donors were isolated by Ficoll-Hypaque dis-continuous gradient centrifugation at 1,000× g for 30 minutes, washed twice in PBS and pelleted at 300× g for 10 minutes. Before infection, the cells were stimulated by phytohemagglutinin (PHA) at a concentration of 6 μg/ml for three days in RPMI 1640 medium supplemented with 15% heat-inactivated fetal calf serum, 1.5 mM L-glutanine, penicillin (100 U/ml), streptomycin (100 μg/ml), and sodium bicarbonate buffer. most of the antiviral assays described below were performed with cells from at least two different donors.

HIV-1 (strain IAV-1) was obtained from the Centers for Disease Control, Atlanta, and propagated in PHA-stimulated human PBM cells using RPMI 1640 medium as above without PHA and supplemented with 7% interleukin-2 (Advanced Biotechnologies, Silver Spring, Md.), 7 μg/ml DEAE-dextran (Phatrnacia, Uppsala, Sweden), and 370 U/ml anti-human leukocyte (alpha) interferon (ICN, Lisle, Ill.). Virus was obtained from the cell free culture supernatant and stored in aliquots at −70° C. until used.

Uninfected PHA-stimulated human PBM cells were uniformly distributed among 25 cm³ flasks to give a 5 ml suspension containing about 2×10⁶ cells/ml. Suitable dilutions of HIV were added to infect the cultures so that the mean reverse transcriptase (RT) activity of the inocula was 50,000 dpm/ml, which was equivalent to about 100 $TCID_{50}$, determined as described in *AIDS Res. Human Retro,* 3: 71–85 (1987). The drugs, at twice their final concentrations in 5 ml of RPMI 1640 medium, supplemented as described above, were added to the cultures. Uninfected and treated PBM cells were grown in parallel as controls. The cultures were maintained in a humidified 5% $CO_2$-95% air incubators at 37° C. for five days after infection, at which point all cultures were sampled for supernatant RT activity. Previous studies indicate that the maximum RT levels are obtained at that time.

The RT assay was performed by a modification of the Spira et al., *J. Clin. Microbial.,* 25, 97–99 (1987) method in 96well microliter plates. The radioactive cocktail (180 μl), which contained 50 mM Tris-HCl pH 7.8, 9 MM $MgCl_2$, 5 mM dithiothreitol 4.7 μg/ml $(rA)_s.(dT)_{12-18}$, 140 μM dATP and 0.22 μM [³H]TTP (specific activity 78.0 Ci/mmol, equivalent to 17,300 cpm/pmol; KEN Research Products, Boston, Mass.), was added to each well. The sample (20 μl) was added to the reaction mixture and incubated at 37° C. for two hours. The reaction was terminated by the addition of 100 μl cold 10% trichloroacetic acid (TCA) containing 0.45 mM sodium pyrophosphate. The acid insoluble nucleic acid which precipitated was collected on glass filters using a Skatron semiautomatic harvester (setting 9). The filters were washed with 5% TCA and 70% ethanol, dried, and placed in scintillation vials. Four ml of scintillation fluid (Econofluor, NEN Research Products, Boston Mass.) was added and the amount of radioactivity in each sample determined using a Packard Tri-Carb liquid scintillation analyzer (model 2,OOOCA). The results were expressed in dpm/mi of original clarified supernatant. The antiviral activity, expressed as the micromolar concentration of compound that inhibits replication of the virus by 50% ($EC_{50}$), was calculated by determining the percent inhibition by the median effect method described in Chou and Talalay, *Adv. Enz Regul.,* 22: 27–55 (1984).

Methodology for Testing Toxicity and Inhibition of Cell Proliferation

The compounds were evaluated for their potential toxic effects on uninfected PRA-stimulated human PBM cells and also in CEM (T-lymphoblastoid cell line obtained from ATCC, Rockville, Md.) and Vero (African Green Monkey kidney) cells. PBM cells were obtained from whole blood of healthy HIV and hepatitis-B seronegative volunteers and collected by a single-step FicolHypaque discontinuous gradient centrifugation. The CEM cells were maintained in RPMI 1640 medium supplemented with 20% heat inactivated fetal calf serum, penicillin (100 U/ml), and streptomycin (100 µg/ml). Flasks were seeded so that the final cell concentration was $3 \times 10^5$ cells/ml. The PBM and CEM cells were cultured with and without drug for 6 days at which time aliquots were counted for cell proliferation and viability using the trypan blue-exclusion method (Sommadossi et al, *Antimicrob. Agents Chemother.*, 32: 997–1001 (1988). Only the effects on cell growth are reported because these correlated well with cell viability. The toxicity of the compounds in Vero cells was assessed after 3 days of treatment with a hemacytometer as described in Schinazi et al, *Antimicrobe Agents Chemother.*, 22: 499–507 (1982). The toxicity, expressed as the micromolar concentration of compound that inhibits the growth of normal cells by 50% ($IC_{50}$), was determined, similarly to $EC_{50}$, by the method of Chou and Talalay.

EXAMPLE 2

Antiviral and Cytotoxicity Assays of 1,3-Dioxolane Nucleosides

Table 1 below lists the results of anti-HIV-1 activity in human PBM cells and toxicity assays in human PBM cells, Vero (African Green Monkey kidney) cells, and CEM cells for 2'-deoxy-3'-oxacytidine (DOC), 2'-deoxy-3'-oxathymidine (DOT), 2'-deoxy-5-fluoro-3'-oxacytidine (FDOC) and 2'-deoxy-5-fluoro-3'-oxauridine (FDOU).

TABLE 1

| Antiviral Drug | ANTI-HIV ACTIVITY | | CYTOTOXICITY | |
|---|---|---|---|---|
| | $EC_{50}$ µM (PBM) | $IC_{50}$ µM (PBM) | $IC_{50}$ µm (Vero) | $IC_{50}$ µM (CEM) |
| Doc | 0.0047 | >200 | 0.17 | <1 |
| DOT | 0.09 | >100 | >100 | |
| FDOC | 0.0063 | >200 | <0.1 | <1 |
| FDOU | >10 | >200 | >100 | >100 |

TABLE 1-continued

| Antiviral Drug | ANTI-HIV ACTIVITY | | CYTOTOXICITY | |
|---|---|---|---|---|
| | $EC_{50}$ µM (PBM) | $IC_{50}$ µM (PBM) | $IC_{50}$ µm (Vero) | $IC_{50}$ µM (CEM) |
| FDOC(+) | 0.027 | | | |
| FDOC(−) | 0.013 | | | |

This invention has been described with reference to its preferred embodiments. Variations and modifications of the invention, will be obvious to those skilled in the art from the foregoing detailed description of the invention. It is intended that all of these variations and modifications be included within the scope of the appended claims.

We claim:

1. (±)-2'-Deoxy-5-fluoro-3'-oxacytidine.
2. (−)-β-2'-Deoxy-5-fluoro-3'-oxacytidine as a resolved enantiomer.
3. (+)-β-2'-Deoxy-5-fluoro-3'-oxacytidine as a resolved enantiomer.
4. A pharmaceutical composition that comprises 2'-deoxy-5-fluoro-3'-oxacytidine, its (−) or (+) enantiomer or a pharmaceutically acceptable salt thereof in combination with a pharmaceutically acceptable carrier.
5. A method for the treatment of HIV infection in human cells, comprising administering an HIV-effective amount of β-2'-deoxy-5-fluoro-3'-oxacytidine or its pharmaceutically acceptable salt, optionally in a pharmaceutically acceptable carrier.
6. A method for the treatment of HIV infection in human cells, comprising administering an HIV-effective amount of (+)-β-2'-deoxy-5-fluoro-3'-oxacytidine as a resolved enantiomer or its pharmaceutically acceptable salt, optionally in a pharmaceutically acceptable carrier.
7. A method for the treatment of HIV infection in human cells, comprising administering an HIV-effective amount of (−)-β-2'-deoxy-5-fluoro-3'-oxacytidine as a resolved enantiomer or its pharmaceutically acceptable salt, optionally in a pharmaceutically acceptable carrier.

* * * * *